(12) United States Patent
Cannon (10) Patent No.: US 8,317,513 B1
(45) Date of Patent: Nov. 27, 2012

(54) ORTHODONTIC ATTACHMENT BONDING TOOL AND METHOD OF USING SAME

(76) Inventor: James L. Cannon, Murrayville, GA (US)

(*) Notice: Subject to any disclaimer, the term of this patent is extended or adjusted under 35 U.S.C. 154(b) by 0 days.

(21) Appl. No.: 13/161,064

(22) Filed: Jun. 15, 2011

(51) Int. Cl.
*A61C 3/00* (2006.01)
*A61C 3/14* (2006.01)
*A61C 5/00* (2006.01)

(52) U.S. Cl. ............ 433/24; 433/29; 433/159; 433/215

(58) Field of Classification Search ............ 433/29, 433/159–160, 24, 215; 294/99.2; 606/210–211; 81/300–427.5
See application file for complete search history.

(56) References Cited

U.S. PATENT DOCUMENTS

| | | | |
|---|---|---|---|
| 3,916,909 A * | 11/1975 | Kletschka et al. | 604/35 |
| 5,049,068 A * | 9/1991 | Sterrett et al. | 433/9 |
| 7,677,888 B1 * | 3/2010 | Halm | 433/29 |
| 2007/0054230 A1 * | 3/2007 | Brezniak | 433/24 |
| 2007/0224571 A1 * | 9/2007 | Watson | 433/31 |

* cited by examiner

*Primary Examiner* — Heidi M Eide
(74) *Attorney, Agent, or Firm* — Johnson, Marcou & Isaacs, LLC; Robert E. Richards (57) ABSTRACT

The invention includes a dental tool for applying orthodontic attachments to teeth. The tool includes a body having a portion for holding the dental tool and a portion for selectively gripping an object to be bonded to a tooth. The tool also includes a nozzle for emitting pressurized air adjacent the portion for selectively gripping the object to be bonded to the tooth. A method of using the tool is also disclosed.

13 Claims, 8 Drawing Sheets

ORTHODONTIC ATTACHMENT BONDING TOOL AND METHOD OF USING SAME

FIELD OF THE INVENTION

The present invention generally relates to dental tools. More particularly, this invention relates to a dental tool for grasping and applying objects, such as orthodontic attachment, to teeth. Specifically, the present invention relates to a dental tool for gripping an orthodontic attachment to be bonded to a tooth and also for drying the tooth and curing a photo-curable adhesive used to bond the orthodontic attachment to the tooth. A method of using the dental tool is also disclosed.

BACKGROUND OF THE INVENTION

In the practice of corrective orthodontia, orthodontic attachments are typically bonded to the labial surface of teeth and metal wires are attached to the attachments to exert forces on the attachments to slowly move the teeth into proper alignment. Examples of orthodontic brackets are shown in U.S. Pat. Nos. 5,512,838; 5,248,257 and 7,329,120 (the disclosures of which are all incorporated herein by reference). The bonding of orthodontic attachments to teeth has been in existence for at least 35 years. The bonding of orthodontic attachments to teeth is typically accomplished with a photo-curable polymeric adhesive or an adhesive whose curing is accelerated or initiated by exposure to light, typically ultraviolet light.

Most adhesives for bonding orthodontic attachments to teeth require a dry environment in order to form a suitable bond with the tooth. Many different systems have been used to remove saliva from the mouth of an orthodontic patient to provide such a dry environment. These systems include saliva removal by way of various vacuum systems, cotton rolls to absorb the saliva, and even small triangular patches to stop the flow of saliva from the saliva ducts. Prescription drugs that stop the flow of saliva have also been used. However, keeping the teeth dry for even a short period of time is especially difficult. Fluid from the gingival tissue tends to ooze constantly onto the surface of the teeth as well as moisture forming on the enamel surface of the teeth as a result of condensation.

Since a dry environment is required for properly bonding orthodontic attachments to teeth, patient preparation time is significant. Furthermore, since it takes a relatively long time to bond orthodontic attachments to all or most of the teeth of a patient, patient comfort is a significant consideration. This consideration is magnified when treating young or teenaged patients. Improved patient comfort usually results in greater patient cooperation, which often results in the bonding procedure being completed in a shorter period of time. Furthermore, if the initial preparation time to produce a dry environment can be avoided, this would also reduce the overall time required for bonding orthodontic attachment.

It would therefore be desirable to provide an orthodontic attachment bonding system that does not require elaborate preparation in order to produce a dry environment in an orthodontic patient's mouth. It would also be desirable to provide an orthodontic attachment bonding system that is more comfortable for the patient. If would further be desirable to provide an orthodontic attachment bonding system that is more efficient and reduces the time required to bond orthodontic attachments to teeth.

SUMMARY OF THE INVENTION

The present invention satisfies the foregoing needs by providing a dental tool for bonding orthodontic attachments, such as orthodontic brackets, buccal tubes, cleats and eyelets, to teeth. The dental tool comprises a tool body having a portion for holding the dental tool and a portion for selectively gripping an object to be bonded to a tooth and a nozzle for emitting pressurized air adjacent the portion for selectively gripping the object to be bonded to the tooth. In a further embodiment, the tool also includes a light source attached to the tool body for curing orthodontic attachment bonding adhesive In an alternate disclosed embodiment, the present invention comprises a method of bonding an object to a tooth. The method comprises holding the object with a portion of a tool adapted therefor, the object having adhesive on a portion thereof, positioning the tool adjacent the tooth, applying pressurized air to the tooth to dry the tooth, the pressurized air being emitted from a portion of the tool and applying the adhesive bearing portion of the object to the dry tooth. In a further embodiment of the invention, the method also includes illuminating the adhesive with light to cure the adhesive, the light being emitted from a portion of the tool.

Accordingly, it is an object of the present invention to provide an improved dental tool for bonding orthodontic attachments to teeth, such as orthodontic brackets, buccal tubes, cleats and eyelets.

Another object of the present invention is to provide a system for bonding orthodontic attachments to teeth that provides greater patient comfort during the procedure.

A further object of the present invention is to provide a system for bonding orthodontic attachments to teeth that is more efficient than present methods.

Another object of the present invention is to provide a dental tool that can both dry a tooth and apply an orthodontic attachment for bonding thereto.

Yet another object of the present invention is to provide a dental tool that can dry a tooth, apply an orthodontic attachment for bonding thereto and cure photo-curable adhesive.

Another object of the present invention is to provide an orthodontic attachment bonding system that does not require drying of the oral cavity prior to application of orthodontic attachments.

These and other objects, features and advantages of the present invention will become apparent after a review of the following detailed description of the disclosed embodiments and the appended drawing and claims.

DETAILED DESCRIPTION OF THE DISCLOSED EMBODIMENTS

As used herein, the terms "cure", "curing" and variations thereof as applied to the term "adhesive" includes both curing all or a portion of the adhesive and/or initiating the curing of the adhesive.

Figure 1:
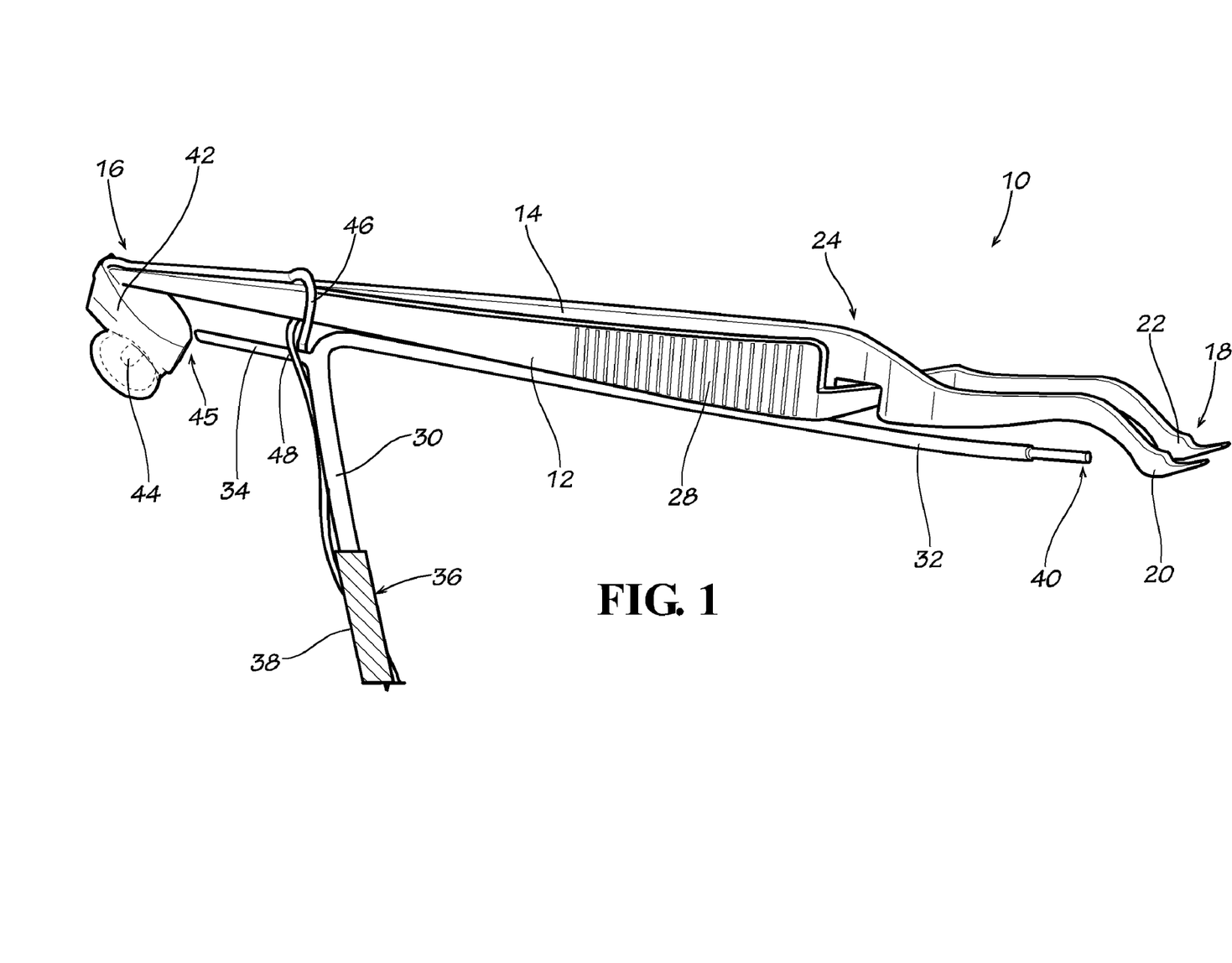
FIG. 1 is a perspective view of a disclosed embodiment of the dental tool of the present invention.
Figure 2:
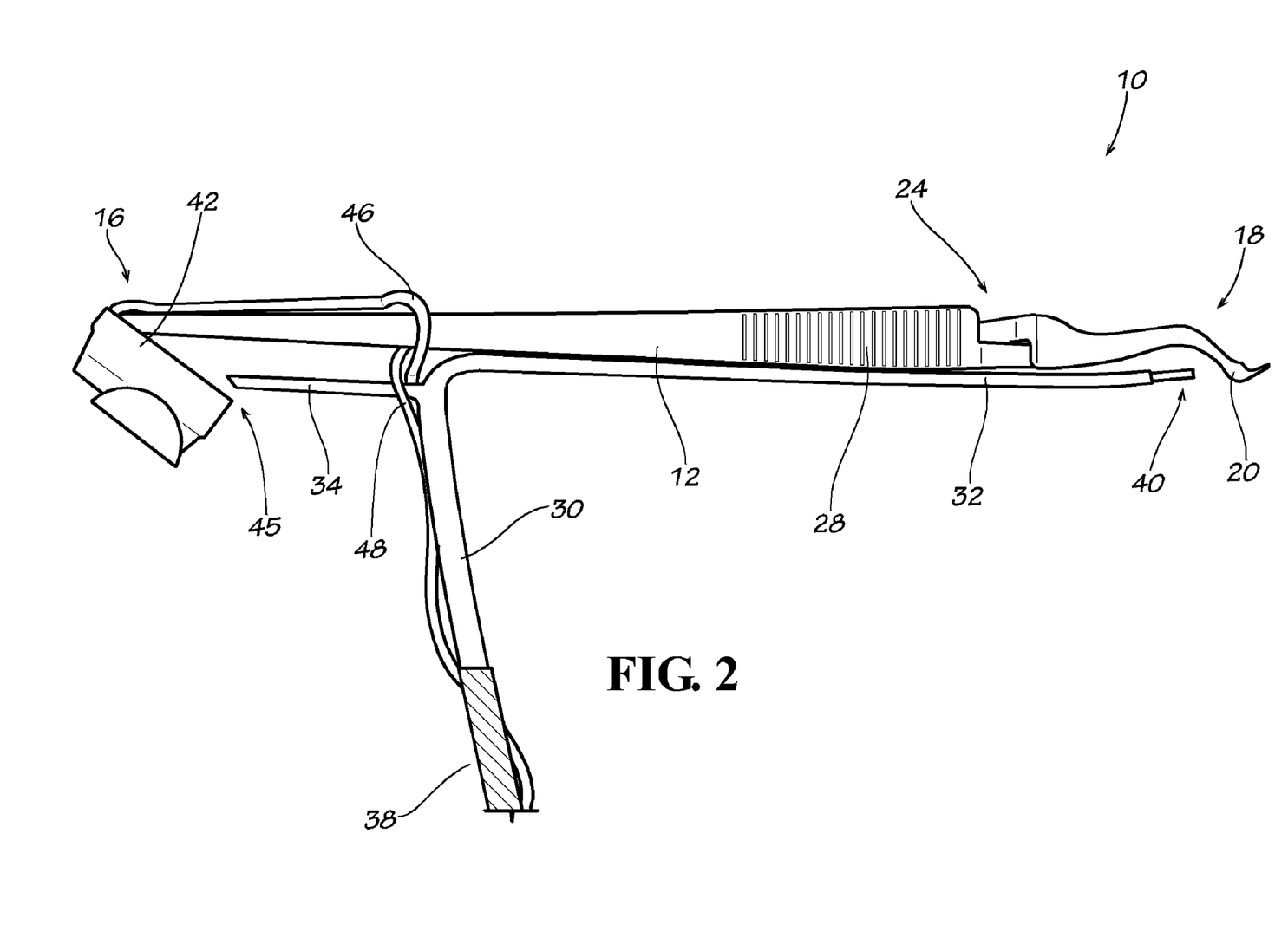
FIG. 2 is a side view of the dental tool shown in FIG. 1.
Figure 3:
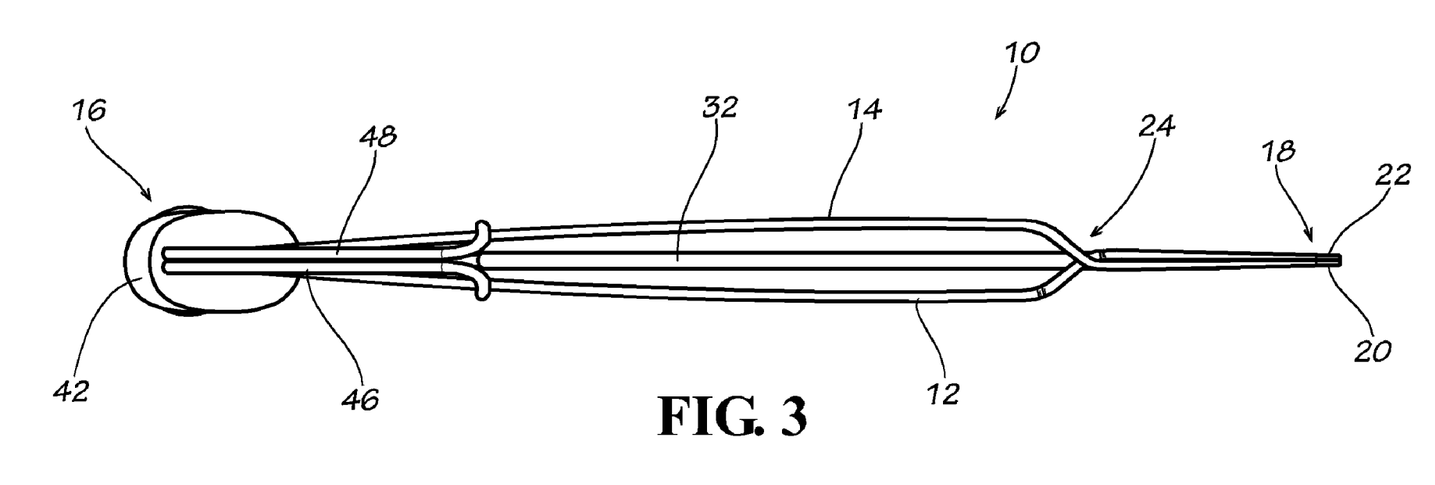
FIG. 3 is a top plan view of the dental tool shown in FIG. 1.
Figure 4:
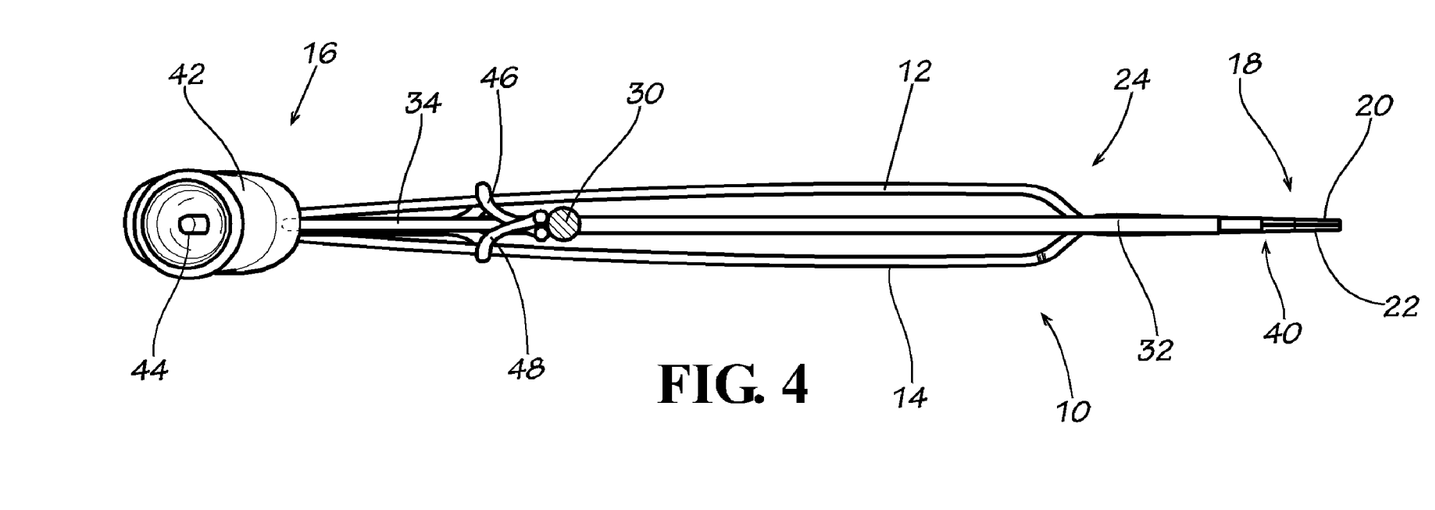
FIG. 4 is a bottom plan view of the dental tool shown in FIG. 1.
Figure 5:
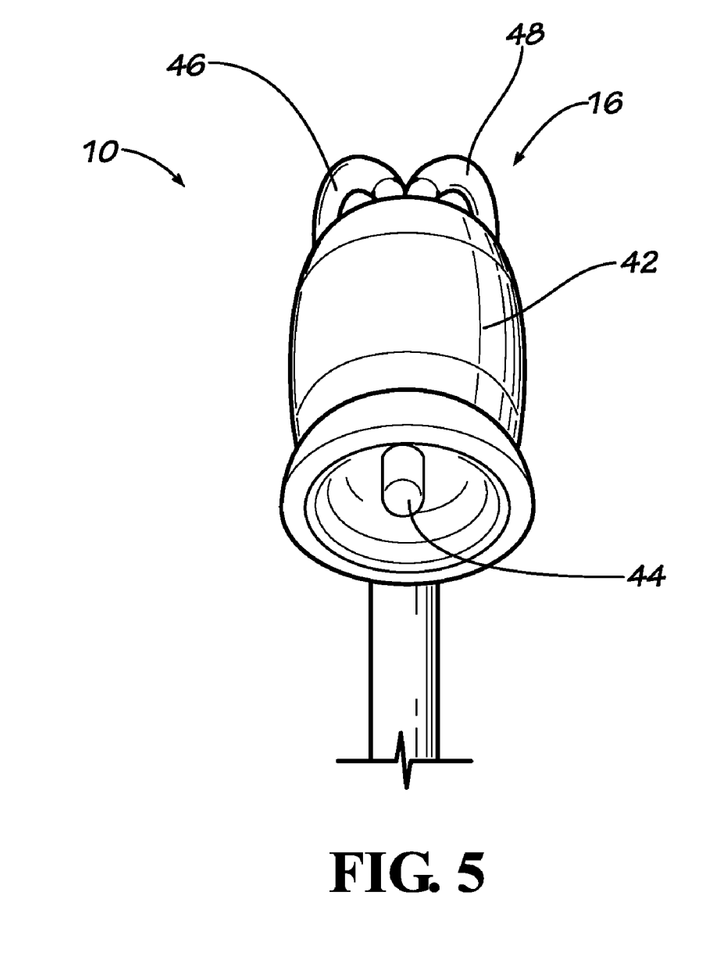
FIG. 5 is a rear end view of the dental tool shown in FIG. 1.
Figure 6:
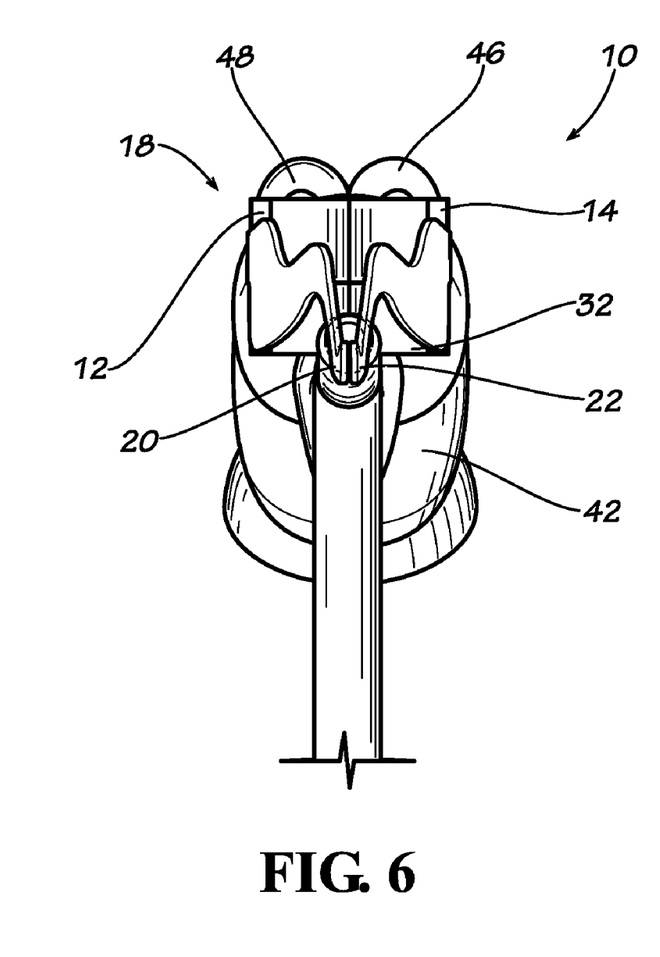
FIG. 6 is a front end view of the dental tool shown in FIG. 1.
Figure 7:
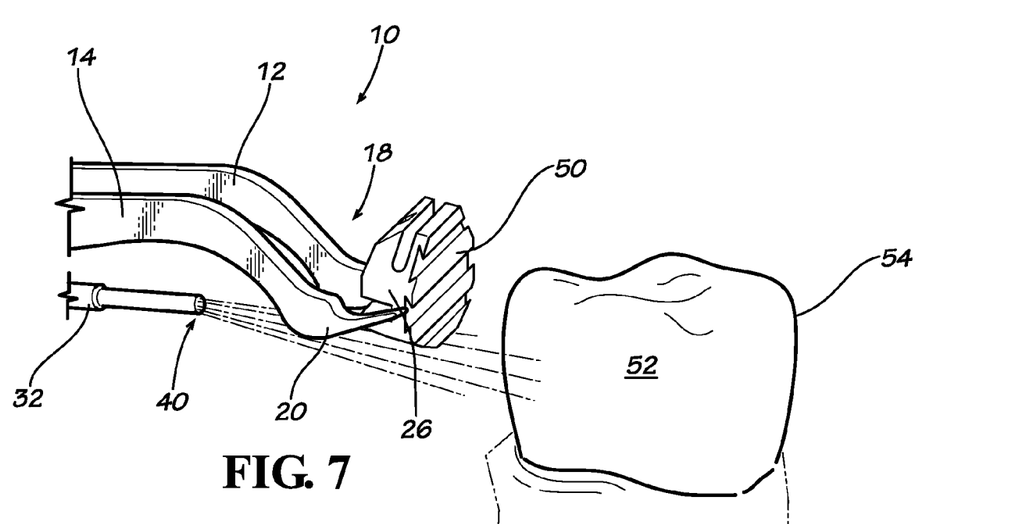
FIG. 7 is a partial close up perspective view of the dental tool shown in FIG. 1 showing the tool holding an orthodontic bracket adjacent a tooth to which the orthodontic bracket is to be attach showing the tooth being dried with pressurized air from the dental tool.

Referring now to the drawing in which like numbers indicate like elements throughout the several views, there is shown in FIG. 1 a disclosed embodiment of an orthodontic attachment bonding tool 10 in accordance with the present invention. Orthodontic attachments include, but are not limited to, orthodontic brackets, buccal tubes, cleats and eyelets. The orthodontic attachment bonding tool 10 comprises orthodontic attachment placement tweezers. In the embodiment shown in FIG. 1 the tweezers are reverse action tweezers; i.e., the tweezers are squeezed to open the jaws and released to close the jaws. Normal action tweezers can also be used; i.e., the tweezers are squeezed to close the jaws and released to open the jaws. Pliers can also be used, although tweezers are preferred. In fact, any tool that is capable of selectively gripping, or otherwise holding, an orthodontic attachment for placement on a tooth is suitable for use in the present invention. The orthodontic attachment bonding tool 10 comprises a pair of elongate stainless spring steel members 12, 14. The spring members 12, 14 are joined together at the rear end 16 of the tool 10, such as by welding. The front end 18 of the members 12, 14 form the jaws 20, 22 of the tool 10. Intermediate the front end 18 and the rear end 16 of the tool 10, the members 12, 14 are bent, such as at 24, so that the members cross over each other. From the bend 24 to the front end 18 of the tool 10, the members 12, 14 are of a reduced width and taper from the bend to the jaws 20, 22. The jaws 20, 22 are sized and shaped so that they are adapted to grip or hold an orthodontic bracket 26 (FIG. 7). The tool 10 can be operated by squeezing the members 12, 14 together, such as between a finger and thumb of an operator's hand placed on the knurled portion 28 of the members 12, 14, causing the jaws 20, 22 to move away from each other; i.e., open the jaws of the tweezers (FIG. 1 shows the jaws in the open position). Releasing the squeezing pressure on the members 12, 14 causes the jaws 20, 22 to move toward each other; i.e., close the jaws of the tweezers (FIGS. 3 and 4 show the jaws in the closed position). A tool of the configuration described above is typical of reverse action orthodontic attachment tweezers and tweezers as described above are commercially available under the designation Model No. 094-x from OrthoPli of Philadelphia, Pa.; Item #8019 and #8016 from Dental Corporation of America of West Chester, Pa.; and Article No. 3503 from Orthodontixx.com. Normal action tweezers are commercially available under the designation TDI-00-SA, from TDI International of Tucson, Ariz.

The tweezers described above are modified as follows to provide a tool 10 in accordance with the present invention. Attached to the bottom of the tool 10 is a small round hollow stainless steel tube 30. The tube 30 branches into a forwardly extending round hollow stainless steel tube 32 and a rearwardly extending round hollow stainless steel tube 34. Attached to the end 36 of the tube 30 is a flexible hose 38 made from rubber or a flexible polymer material. The other end (not shown) of the hose 38 is attached to a source of dry, pressurized air (not shown), which is typically available in an orthodontist's or dentist's office. The end 40 of the forwardly extending tube 32 terminates adjacent the jaws 20, 22 and is directed generally to the point where the jaws meet when in the closed position (FIG. 4). The end 40 of the forwardly extending tube 32 provides a nozzle for emitting dry, pressurized air therefrom.

Attached to the rear end 16 of the tool 10 is a light source 42. The light source 42 includes a bulb, fluorescent tube, or light-emitting diode ("LED") 44 for emitting light for curing adhesives used for bonding orthodontic attachments to teeth, preferably ultraviolet light ("UV-light"). Wires 46, 48 connect the bulb, fluorescent tube or LED 44 to a source of electricity (not shown) suitable for energizing the blub, fluorescent tube or LED such that it emits light of a suitable intensity and wavelength for curing adhesive used for bonding orthodontic attachments to teeth. The end 45 of the rearwardly extending round hollow stainless steel tube 34 terminates adjacent the light source 42 and is directed thereon. The end 45 of the rearwardly extending tube 34 provides a nozzle for emitting dry, pressurized air therefrom.

Use of the orthodontic attachment bonding tool 10 will now be considered. An orthodontic bracket 26 is grasped with the tool 10 by squeezing together the knurled portions 28 of the members 12, 14 thereby opening the jaws 20, 22, positioning the orthodontic bracket between the open jaws and allowing the jaws to close thereby capturing the orthodontic bracket between the jaws of the tool. A quantity of light-curable adhesive, preferably UV-curable adhesive, is the applied to the rear surface 50 of the orthodontic bracket 26 that will be applied to the labial surface 52 of a tooth 54 to which the orthodontic bracket is to be attached. Using a remote foot switch (not shown) to operate a valve (not shown) dry, pressurized air flows through the flexible tube 38, through the tube 30 and through both the forwardly extending tube 32 and the rearwardly extending tube 34. The dry, pressurized air then flows out of the end 40 of the forwardly extending tube 32 and also out of the end 45 of the rearwardly extending tube 34. The tool 10 holding the orthodontic bracket 26 between the jaws 20, 22 is positioned adjacent the tooth 54 (FIG. 7) such that dry, pressurized air flowing out of the end 40 of the forwardly extending tube 32 is directed onto the surface 52 of the tooth 54. No initial preparation or drying of the oral cavity is required prior to attaching an orthodontic attachment when practicing the present invention. The dry, pressurized air flowing from the end 40 of the tube 32 onto the surface 52 of the tooth 54 pushes saliva on the tooth's surface away from the position where the orthodontic bracket is to be attached and the remaining thin layer of saliva on the tooth's surface is dried by the flow of air flowing over it. After sufficient dry, pressurized air has been applied to the tooth 54 such that the surface 52 thereof is dry, the orthodontic bracket 26 is applied to the tooth such that the adhesive-bearing surface 50 of the orthodontic bracket contacts the surface of the tooth. Since the dry, pressurized air from the end 40 of the tube 32 flows onto the surface 52 of the tooth 54 as the bracket 26 is placed on the tooth; the surface of the tooth is maintained in a dry state as the orthodontic bracket is placed thereon. After the orthodontic bracket 26 is placed on the tooth, the jaws 20, 22 of the tool 10 are opened to release the orthodontic bracket therefrom. If necessary, the pointed tips of the jaws 20, 22 can then be used to scrape any excess adhesive from the periphery of the orthodontic bracket 26 and/or from the tooth 54. Again, since dry, pressurized air from the end 40 of the tube 32 continues to flow onto the surface 52 of the tooth 54 during this scraping operation, the tooth and orthodontic bracket 26 are maintained in a dry state.

Figure 8:
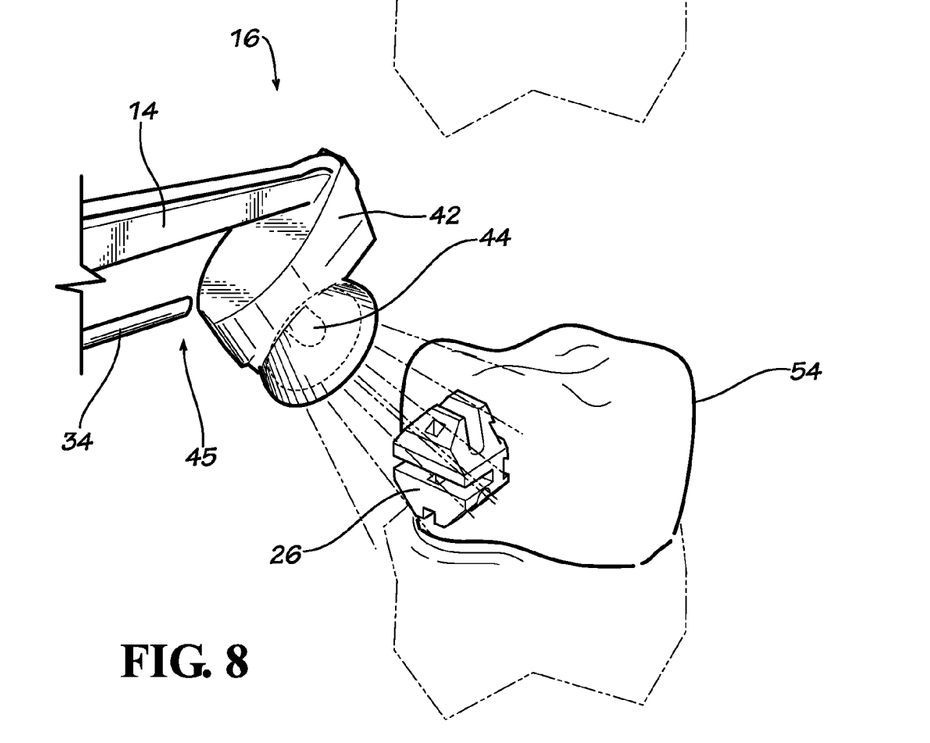
FIG. 8 is a partial close up view of the dental tool shown in FIG. 1 showing the tool adjacent a tooth with an orthodontic bracket attached thereto showing the orthodontic bracket being exposed to light from the dental tool.

The tool 10 is then turned around such that the rear end 16 of the tool, which includes the light source 42, is positioned adjacent the tooth 54 (FIG. 8). The bulb, fluorescent tube, or LED 44 is then energized, such as by activating a footswitch (not shown), so that light from the light source 42, preferably UV-light, shines on and illuminates the adhesive holding the orthodontic bracket 26 on the tooth 54. The light from the light source 42 is shown on the orthodontic bracket 26 for a time sufficient to cure the adhesive thereby bonding the orthodontic bracket to the tooth 54. While the light from the light source 42 illuminates the orthodontic bracket 26 and tooth 54, air flowing from the end 45 of the tube 34 cools the light source 42 so that it does not get too hot.

Figures 9, 10:
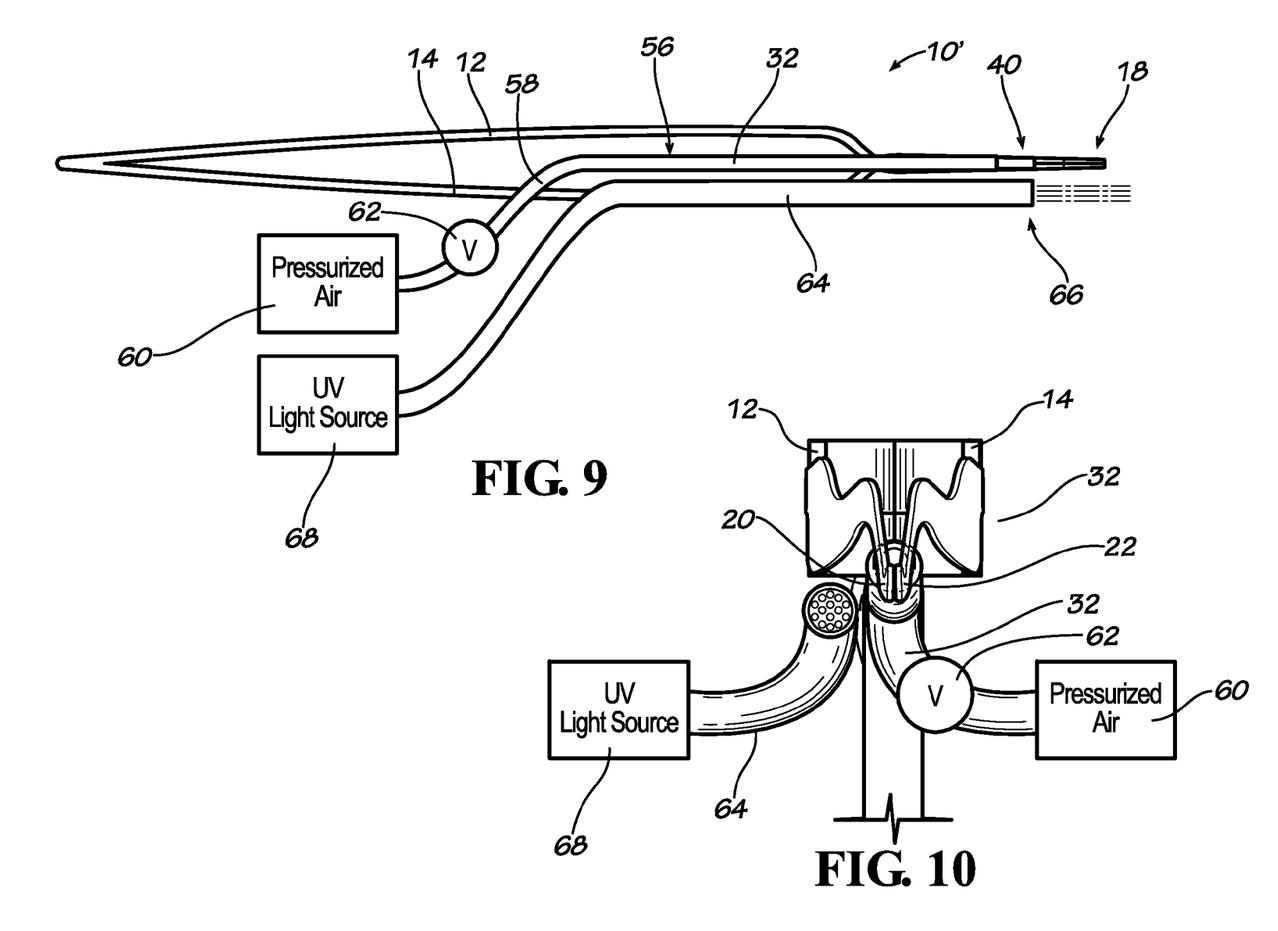
FIG. 9 is a bottom plan view of an alternate disclosed embodiment of the dental tool of the present invention.
FIG. 10 is a front view of the dental tool shown in FIG. 9.

FIGS. 9 and 10 show an alternate disclosed embodiment of the orthodontic bonding tool 10' of the present invention. In this embodiment, the same tweezers are used as described above and shown in FIG. 1. The same forwardly extending round hollow stainless steel tube 32 is used, however the end 56 of the tube 32 opposite the end 40 is connected to a flexible hose 58, which is connected to a source of dry, pressurized air 60. A valve 62 selectively connects the hose 58 and tube 32 to the source of pressurized air 60. Attached to the tweezers adjacent to the tube 32 is a fiber optical cable 64. The end 66 of the fiber optic cable 64 is adjacent the end 40 of the tube 32. The end of the fiber optic cable 64 opposite the end 66 is attached to a source of light 68, such as a bulb, fluorescent tube or LED (not shown) that emits visible light or UV-light. The source of light 68 is connected to a power source (not shown) sufficient for energizing the source of light. A switch (not shown) allows and operator to turn the source of light on and off. The fiber optic cable 64 is connected to the source of light 68 so that light from the source of light is conducted through the fiber optic cable and emitted from the end 66 thereof. Preferably, the source of light 68 is a source of UV-light and the fiber optic cable 64 will conduct UV-light. The source of light 68 is of an intensity and wavelength such that the light emitted from the end 66 of the fiber optic cable 64 is sufficient to cure adhesives used to attach orthodontic attachments to teeth.

Use of the orthodontic attachment bonding tool 10' will now be considered. An orthodontic bracket 26 is grasped with the tool 10' by opening the jaws 20, 22, positioning the orthodontic bracket between the open jaws and allowing the jaws to close thereby capturing the orthodontic bracket between the jaws of the tool. A quantity of light-curable adhesive, preferably UV-curable adhesive, is applied to the rear surface 50 of the orthodontic bracket 26 that will be applied to the labial surface 52 of a tooth 54 to which the orthodontic bracket is to be attached. Using a remote foot switch (not shown) to operate the valve 62 dry, pressurized air flows through the flexible tube 58 through the forwardly extending tube 32. The dry, pressurized air then flows out of the end 40 of the forwardly extending tube 32. The tool 10' holding the orthodontic bracket 26 between the jaws 20, 22 is positioned adjacent the tooth 54 such that dry, pressurized air flowing out of the end 40 of the forwardly extending tube 32 is directed onto the surface 52 of the tooth 54. No initial preparation of the oral cavity is required when practicing this alternate disclosed embodiment of the present invention. The dry, pressurized air flowing from the end 40 of the tube 32 onto the surface 52 of the tooth 54 pushes saliva on the tooth's surface away from the position where the orthodontic bracket 26 is to be attached and the remaining thin layer of saliva on the tooth's surface is dried by the flow of air flowing over it. After sufficient dry, pressurized air has been applied to the tooth 54 such that the surface 52 thereof is dry, the orthodontic bracket 26 is applied to the tooth such that the adhesive-bearing surface 50 of the orthodontic bracket contacts the surface of the tooth. Since the dry, pressurized air from the end 40 of the tube 32 flows onto the surface 52 of the tooth 54 as the bracket 26 is placed on the tooth; the surface of the tooth is maintained in a dry state as the orthodontic bracket is placed thereon. After the orthodontic bracket 26 is placed on the tooth 54, the jaws 20, 22 of the tool 10 are opened to release the orthodontic bracket therefrom. If necessary, the pointed tips of the jaws 20, 22 can then be used to scrape any excess adhesive from the periphery of the orthodontic bracket 26 and/or from the tooth 52. Again, since dry, pressurized air from the end 40 of the tube 32 continues to flow onto the surface 52 of the tooth 54 during this scraping operation, the tooth and orthodontic bracket 26 are maintained in a dry state. The UV-light source 68 is then energized, such as by activating a footswitch (not shown), so that light from the light source 68 is emitted from the end 66 of the fiber optic cable 64 and shines on and illuminates the UV-curable adhesive holding the orthodontic bracket 26 on the tooth 54. Dry, pressurized air from the end 40 of the tube 32 continues to be directed onto the surface 52 of the tooth and orthodontic bracket 26 while the light from the end 66 of the fiber optic cable 64 illuminates the light-curable adhesive on the orthodontic bracket and tooth. The light from the fiber optic cable 66 is shown on the orthodontic bracket 26 for a time sufficient to cure the adhesive thereby bonding the orthodontic bracket to the tooth 54. While the light from the fiber optic cable 64 illuminates the orthodontic bracket 26 and tooth 54, air flowing from the end 40 of the tube 32 keeps the surface 52, adhesive and orthodontic bracket 26 dry thereby improving the bonding strength of the adhesive. In this embodiment, light and pressurized air can be emitted either simultaneously or alternately from the gripping end 18 of the tweezers.

Figure 11:
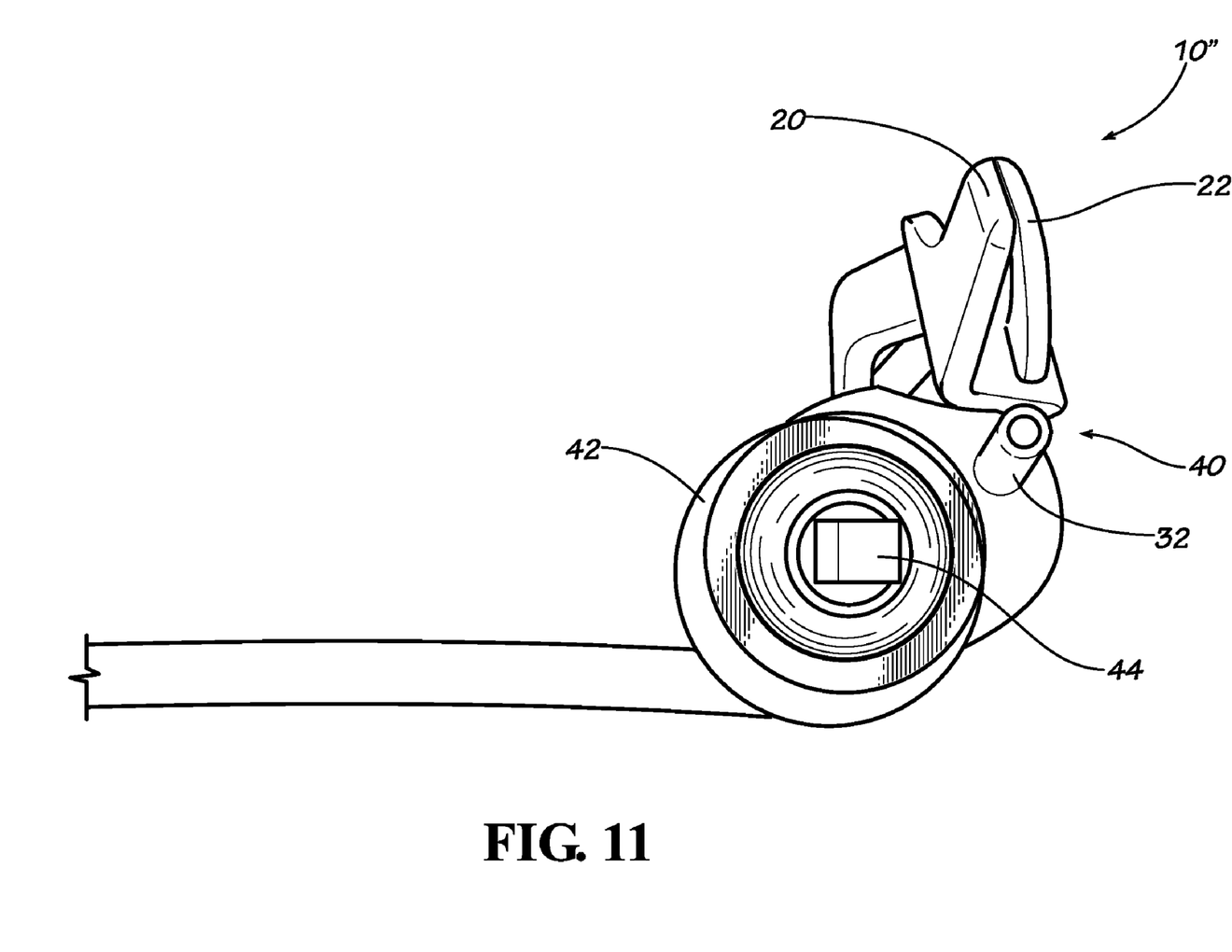
FIG. 11 is a front view of an alternate disclosed embodiment of the dental tool of the present invention.

FIG. 11 shows an alternate disclosed embodiment of the orthodontic bonding tool 10" of the present invention. In this embodiment, the same tweezers are used as described above and shown in FIG. 1. The difference between the embodiment shown in FIG. 11 and the embodiment shown in FIGS. 1-8 is that the light source 42 is moved from the rear end 16 of the tool 10" to the front end 18 of the tool and the rearwardly extending tube 34 is not used. Therefore, in the embodiment shown in FIG. 11, the light source 42 is mounted to the tool 10" adjacent the end 40 of the tube 32.

Use of the orthodontic attachment bonding tool 10" will now be considered. An orthodontic bracket 26 is grasped with the tool 10" by opening the jaws 20, 22, positioning the orthodontic bracket between the open jaws and allowing the jaws to close thereby capturing the orthodontic bracket between the jaws of the tool. A quantity of light-curable adhesive, preferably UV-curable adhesive, is the applied to the rear surface 50 of the orthodontic bracket 26 that will be applied to the labial surface 52 of a tooth 54. Using a remote foot switch (not shown) to operate a valve (not shown) dry, pressurized air flows through the flexible tube 38 and through the forwardly extending tube 32. The dry, pressurized air then flows out of the end 40 of the forwardly extending tube 32. The tool 10" holding the orthodontic bracket 26 between the jaws 20, 22 is positioned adjacent the tooth 54 such that dry, pressurized air flowing out of the end 40 of the forwardly extending tube 32 is directed onto the surface 52 of the tooth 54. No initial preparation of the oral cavity is required when practicing this alternate disclosed embodiment of the present invention. The dry, pressurized air flowing from the end 40 of the tube 32 onto the surface 52 of the tooth 54 pushes saliva on the tooth away from the position where the orthodontic bracket 26 is to be attached and the remaining thin layer of saliva on the tooth's surface is dried by the flow of air flowing over it. After sufficient dry, pressurized air has been applied to the tooth 54 such that the surface 52 thereof is dry, the orthodontic bracket 26 is applied to the tooth such that the adhesive-bearing surface 50 of the orthodontic bracket contacts the surface of the tooth. Since the dry, pressurized air from the end 40 of the tube 32 flows onto the surface 52 of the tooth 54 as the orthodontic bracket 26 is placed on the tooth, the surface of the tooth is maintained in a dry state as the orthodontic bracket is placed thereon. After the orthodontic bracket 26 is placed on the tooth 54, the jaws 20, 22 of the tool 10" are opened to release the orthodontic bracket therefrom. If necessary, the pointed tips of the jaws 20, 22 can then be used to scrape any excess adhesive from the periphery of the orthodontic bracket 26 and/or from the tooth 52. Again, since dry, pressurized air from the end 40 of the tube 32 continues to flow onto the surface 52 of the tooth 54 during this scraping operation, the tooth and orthodontic bracket 26 are maintained in a dry state. The end 18 of the tool 10" is positioned adjacent the tooth 54. The UV-light LED 44 of the UV-light source 42 is then energized, such as by activating a footswitch (not shown), so that UV-light light from the LED shines on and illuminates the adhesive holding the orthodontic bracket 26 on the tooth 54. Dry, pressurized air from the end 40 of the tube 32 continues to be directed onto the surface 52 of the tooth and orthodontic bracket 26 while the light from the light source 42 illuminates the UV-curable adhesive on the orthodontic bracket and tooth. The light from the UV-light source 42 is shown on the orthodontic bracket 26 for a time sufficient to cure the adhesive thereby bonding the orthodontic bracket to the tooth 54. While the light from the UV-light source 42 illuminates the orthodontic bracket 26 and tooth 54, air flowing from the end 40 of the tube 32 keeps the surface 52, adhesive and orthodontic bracket 26 dry thereby improving the bonding strength of the adhesive. In this embodiment, light and pressurized air can be emitted either simultaneously or alternately from the gripping end 18 of the tweezers.

Figure 12:
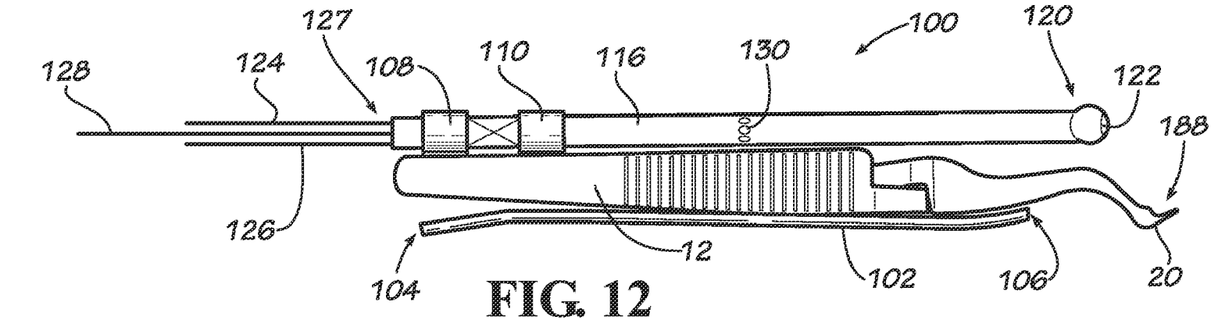
FIG. 12 is a side view of an alternate disclosed embodiment of the dental tool of the present invention.
Figure 13:
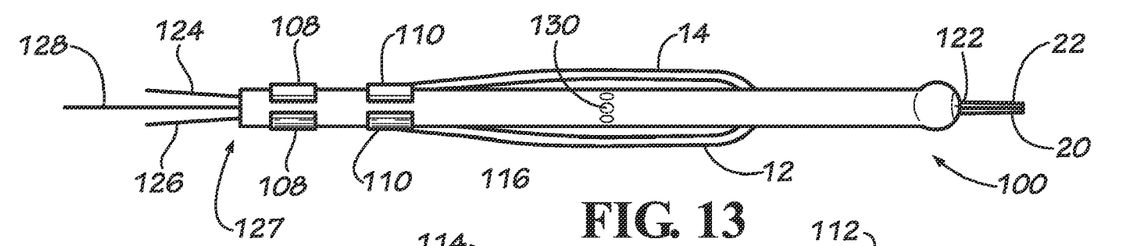
FIG. 13 is a top plan view of the dental toll shown in FIG. 12.
Figure 14:
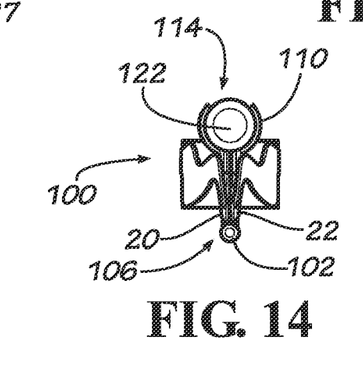
FIG. 14 is a front view of the dental tool shown in FIG. 12.
Figure 15:
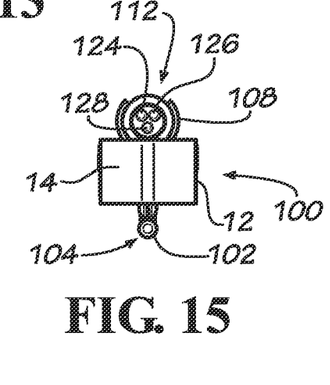
FIG. 15 is a rear view of the dental tool shown in FIG. 12.

With reference to FIGS. 12-15, there is disclosed another alternate embodiment of the present invention. FIG. 12 shows an alternate disclosed embodiment of the orthodontic bonding tool 100 of the present invention. In this embodiment, the same tweezers are used as described above and shown in FIG. 1. Attached to the bottom of the tool 100 is a small, round, hollow, elongate, stainless steel tube 102. The tube 102 extends from the rear end 16 of the tool 100 to the front end 188 of the tool. The tube 102 is attached to the tweezers, such as by welding or soldering, the tube to the pair of elongate stainless spring steel members 12, 14 adjacent the rear end 16 of the tool 100. The rear end 104 of the tube 102 is bent slightly downwardly and away from the members 12, 14 so that a flexible hose (not shown) can be attached to the end of the tube. The flexible hose (not shown) can be attached to the end 104 of the tube 102 by any suitable coupling, such as by a bayonet-type coupling (not shown). The other end of the flexible hose (not shown) is attached to a source of dry, pressurized air. The front end 106 of the tube 102 terminates adjacent the jaws 20, 22 and is bent slightly upwardly and is directed generally to the point where the jaws meet when in the closed position. Thus, when dry, pressurized air is delivered to the end 104 of the tube 102, the pressurized air will travel through the tube and be expelled from the tube at the end 106 and the pressurized air will be directed generally to the point where the jaws 20, 22 meet when in the closed position.

Attached to the top of the tool 100, adjacent the rear end 16 thereof, are a pair of clips 108, 110. The clips 108, 110 are attached to the tweezers, such as by welding or soldering, the clips to the pair of elongate stainless spring steel members 12, 14 adjacent the rear end 16 of the tool 100. The clips 108, 110 are generally C-shaped and are made from spring steel. Each clips 108, 110 defines and upwardly facing opening 112, 114, respectively. The clips 108, 110 are designed so that a round tube, such as the tube 116, can be inserted into the clips through the openings 112, 114 and the clips will temporarily hold the tube in place on the tool 100. The clips 108, 110 are spaced from each other so as to provide more stability to the tube 116 when it is engaged in the clips. When desired, the tube 116 can be removed from the clips 108, 110 by pulling the tube away from the clips through the openings 112, 114. Thus, the clips 108, 100 provide a way for temporarily attaching the tube 116 to the tool 100 and removing the tube therefrom when desired.

The tube 116, when engaged in the clips 108, 100, extends from adjacent the rear end 16 of the tool 100 to adjacent the front end 18 of the tool. The tube 116 can be made from any rigid material, such as stainless steel or plastic. The portion of the tube 116 that fits between the clips 108, 100 can be of a slightly larger diameter or have bosses formed thereon so that when the tube is engaged in the clips, the tube cannot slide longitudinally forward or backward. The tube 116 is preferably round so that when the tube is engaged in the clips 108, 100, the tube can be rotate about its longitudinal axis by rotating the tube with one's fingers. The tube 116 is hollow. Mounted at the front end 120 of the tube 116 is a light emitting diode 122, which emits either visible light or UV-light. The light emitting diode 122 is connected to one end of a pair of electrical wires 124, 126, which extend from the light emitting diode, through the tube 116 and exit the tube at the rear end 127 thereof. The other end of the electrical wires 124, 126 are connected to a suitable power source and control box (not shown) that is located remote from the tool 100. The electrical wires 124, 126 are flexible so that even though they are connected to the remote power source (not shown), the tool 100 can be manipulated freely.

One end of a flexible hose 128 is positioned inside the tube 116 entering through the rear end 127 thereof. The rear end 127 of the tube 116 is sealed with, for example a polymeric material or polymeric glue so that an air tight seal is formed in the rear end of the tube around the electrical wires 124, 126 and the flexible hose 128. The other end of the flexible hose 128 is connected to a source of dry, pressurized air (not shown). The tube 116 has a plurality of vent holes 130 formed intermediate the opposite ends 120, 127 of the tube. The holes 130 are spaced circumferentially around the tube 116. Therefore, when pressurized air enters the tube 116 from the flexible hose 128 the some of the pressurized air will be vented through the vent holes 130. Air inside the tube 116 adjacent the light emitting diode 122 will be heated by the light emitting diode when it is lit. However, the vent holes will act as a venture and will pull some of the heated air inside the tube adjacent the light emitting diode 122, thereby cooling the light emitting diode.

Use of the orthodontic attachment bonding tool 100 will now be considered. The tool 100 is assembled by first slipping a close fitting clear plastic sheath (not shown) over the end 120 of the tube 116. The plastic sheath is provided for sanitary reasons since autoclaving the light emitting diode 122 is not possible. The sheath will completely cover the light emitting diode 122 and a portion of the tube 166 up to, but not covering, the holes 130. The tube 116 is then attached to the tweezers by pressing the rear portion 127 of the tube into the clips 108, 110. The flexible hose 128 and the electrical wires 124, 126 are already connected to a control box, which selectively provides dry pressurized air to the hose 128, and electricity to the wires as desired by the operator. Another flexible hose (not shown) connected to the control box and source of dry, pressurized air (not shown) is connected to the rear end 104 of the tube 102.

An orthodontic bracket 26 is grasped with the tool 100 by squeezing together the knurled portions 28 of the members 12, 14 thereby opening the jaws 20, 22, positioning the orthodontic bracket between the open jaws and allowing the jaws to close thereby capturing the orthodontic bracket between the jaws of the tool. A quantity of light-curable adhesive, preferably UV-curable adhesive, is the applied to the rear surface 50 of the orthodontic bracket 26 that will be applied to the labial surface 52 of a tooth 54 to which the orthodontic bracket is to be attached. Using a remote foot switch (not shown) to operate a valve (not shown) dry, pressurized air flows through the flexible tube, through the tube 102 and out of the end 106. The tool 100 holding the orthodontic bracket 26 between the jaws 20, 22 is positioned adjacent the tooth 54 (FIG. 7) such that dry, pressurized air flowing out of the end 106 of the tube 102 is directed onto the surface 52 of the tooth 54. No initial preparation or drying of the oral cavity is required prior to attaching an orthodontic attachment when practicing the present invention. The dry, pressurized air flowing from the end 106 of the tube 102 onto the surface 52 of the tooth 54 pushes saliva on the tooth's surface away from the position where the orthodontic bracket is to be attached and the remaining thin layer of saliva on the tooth's surface is dried by the flow of air flowing over it. After sufficient dry, pressurized air has been applied to the tooth 54 such that the surface 52 thereof is dry, the orthodontic bracket 26 is applied to the tooth such that the adhesive-bearing surface 50 of the orthodontic bracket contacts the surface of the tooth. Since the dry, pressurized air from the end 106 of the tube 102 flows onto the surface 52 of the tooth 54 as the bracket 26 is placed on the tooth; the surface of the tooth is maintained in a dry state as the orthodontic bracket is placed thereon. After the orthodontic bracket 26 is placed on the tooth 54, the jaws 20, 22 of the tool 100 are opened to release the orthodontic bracket therefrom. If necessary, the pointed tips of the jaws 20, 22 can then be used to scrape any excess adhesive from the periphery of the orthodontic bracket 26 and/or from the tooth 54. Again, since dry, pressurized air from the end 106 of the tube 102 continues to flow onto the surface 52 of the tooth 54 during this scraping operation, the tooth and orthodontic bracket 26 are maintained in a dry state. Using another footswitch (not shown), the light emitting diode 122 is energized so that light from the light emitting diode, preferably UV-light, shines on and illuminates the adhesive holding the orthodontic bracket 26 on the tooth 54. At the same time that the light emitting diode is energized, pressurized air is delivered to the tube 116 through the flexible hose 128. This air cools the light emitting diode 122 while it is illuminated. The light from the light emitting diode 122 is shown on the orthodontic bracket 26 for a time sufficient to cure the adhesive thereby bonding the orthodontic bracket to the tooth 54. While the light from the light emitting diode 122 illuminates the orthodontic bracket 26 and tooth 54, air flowing from the end 106 of the tube 102 keeps the tooth and orthodontic bracket dry during the curing of the adhesive.

The control box (not shown) contains circuitry such that the light emitting diode 122 will be energized for a desired period of time, such as 10 seconds. If additional curing is necessary, the footswitch (not shown) can be pressed again thereby energizing the light emitting diode 122 for another 10 seconds. This procedure can be repeated as many times as necessary to cure the adhesive on the orthodontic bracket 26. The circuitry in the control box (not shown) will also keep the air flowing through the flexible tube 128 and tube 130 for a period of time, such as 10 seconds, after the light emitting diode 122 is no longer energized; i.e., after the light is turned off, so as to further cool the light emitting diode. Alternately, instead of a footswitch, a key pad can be used by a dental assistant to turn the sir flow and light emitting diode 122 on.

After the adhesive on the orthodontic bracket 26 is cured, the tube 166 is disconnected from the tweezers by pulling the tube out of the clips 108, 110. The plastic sheath on the end of the tube 120 is removed and discarded. The flexible hose (not shown) attached to the rear end 104 of the tube 102 is removed therefrom. The tweezers can then be placed in an autoclave for sterilization for future use.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of bonding an object to a tooth comprising:
   holding the object with a portion of a tool adapted therefor, the object having adhesive on a portion thereof;
   positioning the tool adjacent the tooth, the tool having a portion for emitting pressurized air;
   applying pressurized air from the emitting portion to the tooth to dry the tooth, while the tool is positioned adjacent the tooth; and
   applying the adhesive bearing portion of the object to the dry tooth while continuing to apply pressurized air to the tooth from the emitting portion of the tool.

2. The method of claim 1, wherein the object is an orthodontic bracket, buccal tube, cleat or eyelet.

3. The method of claim 1, wherein the adhesive is a photo-curable adhesive and further comprising illuminating the adhesive with light to cure the adhesive, the light being emitted from a portion of the tool.

4. The method of claim 3, wherein the light is emitted from a portion of the tool adjacent the holding portion of the tool.

5. The method of claim 3, wherein the light and air are emitted from a portion of the tool adjacent the holding portion of the tool.

6. The method of claim 3, wherein pressurized air is applied to the tooth from the emitting portion of the tool while the adhesive is illuminated with the light.

7. The method of claim 3, wherein the light is ultraviolet light.

8. The method of claim 3, further comprising releasing the object from the tool.

9. The method of claim 3, wherein the object is an orthodontic bracket, buccal tube, cleat or eyelet.

10. The method of claim 3 further comprising directing a portion of the pressurized air toward the light-emitting portion of the tool to cool the light-emitting portion.

11. A method of bonding an orthodontic attachment to a tooth comprising:
   gripping the orthodontic attachment with a portion of a gripping tool, the orthodontic attachment having UV-curable adhesive on a portion thereof;
   positioning the gripping tool adjacent the tooth;
   applying sufficient pressurized air to the tooth to dry the tooth, the pressurized air being emitted from a portion of the gripping tool adjacent the gripping portion;

applying the adhesive bearing portion of the orthodontic attachment to the dry tooth while continuing to apply pressurized air to the tooth from the emitting portion of the tool;

releasing the orthodontic attachment from the gripping tool; and illuminating the adhesive with UV-light to cure the adhesive, the UV-light being emitted from a portion of the gripping tool.

12. The method of claim 11, wherein the UV-light is emitted from a portion of the gripping tool adjacent the gripping portion of the tool.

13. The method of claim 11, wherein pressurized air is applied to the tooth while the adhesive is illuminated with UV-light.

* * * * *